US006750256B1

(12) United States Patent
Crandall, Jr. et al.

(10) Patent No.: US 6,750,256 B1
(45) Date of Patent: Jun. 15, 2004

(54) USE OF AROMATIC ALDEHYDES AS INSECTICIDES

(75) Inventors: Bradford G. Crandall, Jr., Davis, CA (US); Ralph W. Emerson, Davis, CA (US)

(73) Assignee: Proguard, Inc., Suisun City, CA (US)

( * ) Notice: Subject to any disclaimer, the term of this patent is extended or adjusted under 35 U.S.C. 154(b) by 0 days.

(21) Appl. No.: 09/431,542

(22) Filed: Oct. 29, 1999

Related U.S. Application Data

(63) Continuation-in-part of application No. 08/860,499, filed as application No. PCT/US95/17007 on Dec. 29, 1995, which is a continuation-in-part of application No. 08/482,222, filed on Jun. 7, 1995, now Pat. No. 5,676,958, which is a continuation-in-part of application No. 08/366,974, filed on Dec. 30, 1994, now Pat. No. 5,536,501.

(51) Int. Cl.$^7$ ............................................. A01N 35/00
(52) U.S. Cl. ........................ 514/701; 514/693; 424/405; 424/406
(58) Field of Search .......................... 424/405, 406; 514/693, 701

(56) References Cited

U.S. PATENT DOCUMENTS

| | | | |
|---|---|---|---|
| 2,465,854 A | 3/1949 | Dorman et al. | |
| 3,236,869 A | 2/1966 | Thompson | |
| 4,193,984 A | 3/1980 | Kydonieus | |
| 4,402,950 A | 9/1983 | Wolf et al. | |
| 4,477,361 A | 10/1984 | Sperti et al. | |
| 4,978,686 A | 12/1990 | Sotome | |
| 5,166,317 A | 11/1992 | Wallace et al. | |
| 5,202,247 A | 4/1993 | Kilburn et al. | 435/195 |
| 5,340,731 A | 8/1994 | Kilburn et al. | |
| 5,639,794 A | 6/1997 | Emerson et al. | |
| 5,653,991 A * | 8/1997 | Rod | 424/406 |
| 5,693,344 A * | 12/1997 | Knight et al. | 424/687 |

FOREIGN PATENT DOCUMENTS

| | | | |
|---|---|---|---|
| DE | 3605753 | * | 8/1987 |
| FR | 2529755 | | 1/1984 |
| GB | 504125 | | 5/1939 |
| GB | 2209943 | | 6/1989 |
| JP | 57120501 | | 7/1982 |
| JP | 59222402 | | 12/1984 |
| JP | 63255203 | | 10/1988 |
| JP | 1261303 | | 10/1989 |
| JP | 3081202 | | 4/1991 |
| JP | 4149103 | | 5/1992 |
| JP | 4176460 | | 6/1992 |
| JP | 50024436 | | 2/1993 |
| JP | 5117125 | | 5/1993 |
| JP | 5139924 | | 6/1993 |
| JP | 6183925 | | 7/1994 |
| SE | 8900902 | * | 3/1989 |
| WO | WO94/24158 | | 10/1994 |
| WO | WO94/27434 | | 12/1994 |
| WO | 97/35476 | * | 10/1997 |

OTHER PUBLICATIONS

Cowles et al Cinnamy C Derivatives J. Chem. Ecology vol. 6 #8, 1990.*

Metcal F Lampman Extragoee Analogues J. Econ. Entomology vol. 82 #1, Feb. 1989.*

Arctander 1653 & 149, 1969.*

Herbert, C.D. et al., "Comparison of the toxicity of cinnamaldehyde when administered by microencapsulation in feed or by corn oil gavage," *Food Chem. Toxicol.* (1994) 32(12):1107–15, (Abstract) Chemical Abstracts, Abstract No. 104321, vol. 122, No. 9, Feb. 27, 1994, Columbus, Ohio, USA.

Ejges, T.A. et al., "Food Aroma Composition Containing Vanillin, Rum Extract, Cinnamic Aldehyde Caramel Ethanol balsam Acetate Propionate Cinnamate," (Abstract) SU 980289 Aug. 1982, Database: Derwent WPI, Acc. No. 83–61046K, Derwent Publications, Ltd., London, GB.

Ottoboni, F. et al., "House dust mites prevention in Italy," *Bollettino di Zoologia Agraria e di Bachiocultura,* (1992) vol. 24, No. 2, pp. 113–120, (Abstract) Database: CABA, No. 94:73423.

Tadeka Chem Ind Ltd., "Insecticidal compositions comprise at leaset one plant extract of Moringa, Marah, Momordica, Sophora, Maackia, Tinospora, Zantoxylum, Piper, Strychnos, Stryax and Liquidambar, water and/or hydrophilic solvent," JP06–329514 A, Nov. 1994 (Abstract), Database: Derwent WPI, Acc. No. 95–048734, Derwent Publications, Ltd., London, GB.

Saotome Kiyoshi, "Protecting crops against insects, microorganisms and pathogenic fungi by applying cinnamic aldehyde emulsion," JP 57–120501 A, Jul. 1982 (Abstract), Database: Derwent WPI, Acc. No. 82–73641E, Derwent Publications, Ltd., London, GB.

Taisho Pharm Co Ltd, "Acaricidal composition to control indoor dust mites—contains (m)ethyl cinnamates, cinnamic alcohol, cannamyl acetate and or substitute cinnamaldehyde," JP 04–149103 A, May 1992 (Abstract), Database: Derwent WPI, Acc. No. 92–223400, Derwent Publications, Ltd., London, GB.

(List continued on next page.)

*Primary Examiner*—Neil S. Levy
(74) *Attorney, Agent, or Firm*—Dorsey & Whitney LLP; David J. Brezner; Diane J. Mason

(57) ABSTRACT

Methods and compositions based upon natural aromatic aldehydes are provided, which find use as pesticides. The pesticides are formulated in a variety of ways, including dusts, sprays, shampoos and soaps, and can be bound to a solid support or provided as bait or directly impregnated into organic matter infested by or susceptible to infestation by a target pest. Pests controlled include mosquitos, lice, ants, cockroaches, lice, and ticks.

1 Claim, No Drawings

OTHER PUBLICATIONS

Otsuka Kagu Kogyo KK, "Insecticide Composition having long–lasting effect—contains volatile insecticide and alcohol," JP 59–222402 A, Dec. 1984 (Abstract), Database: Derwent WPI, Acc. No. 85–027823, Derwent Publications, Ltd., London, GB.

Ogawa & Co., LTD, "Moth–proofing agents—containing trioxanes as carrier for the active ingredient," JP 50–024436 A, Mar. 1975 (Abstract), Database: Derwent WPI, Acc. No. 75–83685W, Derwent Publications, Ltd., London, GB.

Taiyo Koryo KK, "Agent for combating Thysanoptera—containing cinnamic aldehyde as active component," JP 01–261303 A, Oct. 1989 (Abstract), Database: Derwent WPI, Acc. No. 89–351364,. Derwent Publications, Ltd., London, GB.

Tashiro Eiichi, JP 06–183925 A, Jul. 1994 (Abstract), Database: Derwent WPI, Acc. No. 94–252673, Derwent Publications, Ltd., London, GB.

Dainippon Jochugiku Co Ltd., JP 03–081202 A, Apr. 1991 (Abstract), Database: Derwent WPI, Acc. No. 91–144786, Derwent Publications, Ltd., London, GB.

Itouen:KK, "Plant Disease Injury Controlling Agent Containing Natural Ingredient as Active Ingredient," JP 05–139924 A, Jun. 1993 (Abstract), Patent Abstracts of Japan.

Tanaka Tomoji, JP 04–176460 A, Jun. 1992 (Abstract), Database: Derwent WPI, Acc. No. 92–262127, Derwent Publications, Ltd., London, GB.

Bowles & Miller, *J. Food Protection* (1993) *56*:788–794.

Casey & Dobb, *Enzyme Microb. Technol.* (1992) *14*:739–747.

Frear, *Chemistry of Insecticides and Fungicides* (1942) *13*:184–191.

King, *Agriculture Handbook,* (1954) 69:1–397.

Lampman & Metcalf, *Environ. Entomol.* (1988) *17*:644–648.

Lampman & Metcalf, *J.Environ. Entmol.* (1987) *80*:1137–1142.

Lewis et al. (1990) *19*:8–14.

Matsumoto Microbiology Laboratory, *Antimicrobial Test of Avian–M*(1982) *57–07*.

Metcalf and Metcalf, "Insect Ecology and Control" in *Plant Kairomones,* Chapman and Hall (1992), pp. 8, 83, 84, 95, 96 and 157.

Metcalf and Metcalf, "Destructive and Useful Insects: Their Habits and Control" in *Insect Control 5$^{th}$ Edition,* McGraw–Hill, Inc. (1993), pp. 7.58–7.60.

Metcalf and Lampman, *J.Econ. Entmol.* (1989) *82*:1620–1625.

Metcalf and Lampman, *Experientia* (1989) *45*:240–247.

Metcalf and Lampman, *Proc. Natl. Acad. Sci. USA* (1991) *88*:1869–1872.

Yuan et al., *Fundamental and Applied Toxicol.* (1993) *20*:83–87.

The Merck Index Eleventh Edition (1989) (XP002042547).

* cited by examiner

USE OF AROMATIC ALDEHYDES AS INSECTICIDES

CROSS-REFERENCE TO RELATED APPLICATIONS

This application is a continuation-in-part of U.S. Ser. No. 08/860,499, filed Jul. 21, 1997, pending, which is a continuation-in-part of U.S. Ser. No. 08/482,222, filed Jun. 7, 1995, as U.S. Pat. No. 5,676,958, which is a continuation-in-part of U.S. Ser. No. 08/366,974, filed Dec. 30, 1994, issued Jul. 16, 1996 as U.S. Pat. No. 5,536,501, which disclosures are incorporated herein by reference.

INTRODUCTION

TECHNICAL FIELD

The present invention is related to insecticidal and arachnidal compositions containing aromatic aldehydes as essential ingredients and their use in a method for protecting against infestation and attack by insects and arachnids. The method is exemplified by applying an effective amount of a composition which includes cinnamic aldehyde and/or cinnamic aldehyde substituted at the α position with a butyl or a hexyl group in the vicinity of two-spotted spider mites, flies, fleas, ticks, cockroaches, western subterranean termites, ants, mosquitos, lice, biting midges, and earwigs as a means of controlling and/or preventing infestation and attack by these pests.

BACKGROUND

Organic matter, including decaying organic matter, is colonized by a variety of organisms, many of which are dependent upon a particular organic material as a source of nutrients. The colonizing organisms include a variety of insects and arachnids, some of which spread disease and/or damage the material which they colonize. The insects and arachnids which colonize particular organic materials include those species such as cockroaches, fleas, termites and spider mites which are symbiotic with bacteria; the host organism cannot survive without the symbionts. The colonizing organisms also include those which are disease vectors to mammals and include ticks, mites, fleas, and mosquitos and various sap-sucking insects which are disease vectors to plants, and include aphids and thrips. The Prostigmata include sap-sucking plant parasites, the most important of which are the gall mites and spider mites which cause damage to agricultural and horticultural plants around the world.

Most orders of ticks include species of medical importance. Just the activity of the blood-sucking habit of ticks causes irritation and malaise in the host. However, the tick's role as carrier and transmitter of human disease organisms is of most concern medically. The organisms, chiefly viruses, rickettsiae and spirochaeta bacteria, are transmitted in the tick's saliva during feeding, and any one organism can be carried by a range of tick species. The viruses cause hemorrhagic fevers or encephalitis. The habitats of ticks include Canada, the U.S.A., Malaysia, India, and eastern, northern and central Europe. The different types of diseases caused by ticks usually are named after the place where they were first identified (e.g., Omsk hemorrhagic fever).

Another disease risk that is spreading geographically is Lyme disease (LD). LD is a multisystem inflammatory disease that in its early localized form affects the skin and joints, nervous system and, to a lesser extent, other organic systems. Like a virus, rickettsia can develop only inside living cells. The main human rickettsial infections are the spotted fevers, tick-bite fevers and tick-typhus fevers, one of the most famous examples being Rocky Mountain spotted fever, which in the western U.S.A. is carried by the wood tick, Spirochaetes. The disease is characterized in humans by relapsing fevers and is transmitted by tick species of the genus Ornithodoros. These occur in Africa and the Americas.

In cattle, *Ornithodoros coriaceus* has been studied in order to gauge its relationship to bovine abortion. Epizootic Bovine Abortion (EBA) has become recognized as a major factor in preventing maximum range cattle calf production in California. Cows of various ages and breeds are susceptible to the disease, and abortion rates of up to 40 percent are not uncommon. *O. coriaceus* tested for vector ability were captured from EBA enzootic areas in California. After transport to the laboratory and acclimation, heifers were exposed to EBA by blood feeding. A cause and effect relationship between *O. coriaceus* blood feeding and subsequent disease was established. This soft tick disease represents a $30–$50 million problem in the state of California, with catastrophic loss years of approximately $100 million. Another disease vector affecting cattle is the soft tick which is the vector of numerous arboviruses.

Larval mites of the family Trombiculidae, commonly called chiggers or red bugs, are mostly lymph-feeding ectoparasites of vertebrates. About 20 species cause either a dermatitis (scrub-itch), resulting from an allergic reaction to the chigger's saliva, or transmit human disease organisms. Among the latter is the most important of mite-borne diseases, scrub-typhus or tsutsugamushi disease, which occurs in many parts of eastern and southeastern Asia. The best known mites which infect humans are scabies or itch mites. Scabies, known also to be a severe irritant to cattle, is highly contagious and its effects range from dermal irritation to death. Favored sites for infection are the hands and wrists; usually severe itching and rashes result.

House-dust mites induce allergic reactions in the form of asthma and rhinitis in humans. Several species of food mites cause a dermatitis in people handling infested food which include grocer's itch, associated with the presence of the flour mite. The crab louse, head (*Pediculus humans*) and pubic (*Phthirius pubis*), also cause discomfort to humans. Lice act as vector for exanthematous typhus, a disease caused by *Rickettsiaprowazekii*, a rickettsia. Millions of deaths have resulted from this disease. In domestic animals disease and, more importantly, weight loss due to irritation, are caused by lice.

Mosquitoes, because of the pathogenic microorganisms they not only carry around but in some cases actively culture, are an important threat to human health. While particularly adept at transmitting diseases caused by viruses, they also are known vectors of disease-causing nematodes and protozoans. The mosquito species probably the most closely associated with humans is that of the genus Aedes. There are about 150 species of this genus in North America; one, *Aedes vexans*, the inland floodwater mosquito, is known for its painful bite. In terms of human health problems, the most important species of Aedes is *A. aegypti*, which is the vector for an arbovirus that causes the disease yellow fever in humans.

Other arboviruses associated with the Aedes species include those which cause dengne fever; eastern and western encephalitis; Venezuelan equine encephalitis; St. Louis encephalitis; chikungunya; oroponehe and bunyamidera. Given this spectrum of disease, there is justifiable concern over the recent introduction (1985) of *A. albopictus* into the U.S. *A. albopictus* is a known vector of dengue fever and a suspected vector of a number of forms of encephalitis, hemorrhagic fever and yellow fever. The genus Culex contains various species including the common house mosquito, *C. pipiens*. In North America, it is implicated in the transmission of various forms of encephalitis and the filarial worms *Wuchereria banufti* or *Brugia malayi* responsible for elephantiasis. Mosquitoes may also be the vector for Ebola, which is caused by a filovirus.

In the mosquito genus Anopheles, of which there are about 300 species worldwide, 15 species live in North America. While many species of mosquito feed on human blood, a majority of individual mosquitoes in the world do not; for them the consumption of human blood is distasteful and other vertebrate hosts are preferred, to which they spread disease. Certain anopheline mosquitoes can act as vectors of pathogenic organisms that circulate in the bloodstream. Among these are protozoans in the genus Plasmodium, which cause the disease malaria in humans which afflicts between 200 and 300 million people and kills at least two million every year. Humans are affected by only four species of this genus: *P. vivax*, *P. ovale*, *P. malariae* and *P. falciparum*.

Other pests which can act as disease vectors include cockroaches. Cockroaches remain one of the most widespread and troublesome household and commercial pests, in spite of rather extensive use of insecticides. The most pestiferous species of cockroaches in California is *Blattella germanic* (L), the German cockroach. These cockroaches are found in grocery stores, restaurants, hospitals, jails, hotels, apartments, homes, particularly in about any place that food is stored. Most often they are associated with less than adequate sanitary conditions and are linked with the mechanical transmission of several pathogenic microorganisms. The droppings or skins of cockroaches cause hives or rashes, coughing, sneezing and contact or inhalant allergic reactions in humans. Regular insecticide application is the usual means of cockroach control. The common strategy is to spray areas where the insect has been seen or is suspected to dwell. The ability of cockroaches to expand their populations rapidly, their close association with people and food, and their propensity to hide in inaccessible places make it difficult to exterminate them.

Formulations which are used for controlling insect and arachnid pests include the following: organophosphates such as malathion and ditrom; non-organophosphates such as pyrethrum and pyrethroids (synthetic pyrethrum); mineral oil; oil; methoprene; and bacillus thuriengiensis israelensis crystal protein. However, the wide-spread use of pesticides has resulted in the development and evolution of resistant pests, as well as growing environmental and health care concerns about the use of pesticides. As an example, the pesticide registration for malathion may be cancelled when it undergoes the reregistration process at the USEPA; the pesticide registration for DDT was similarly cancelled due to environmental and health care concerns. A highly visible ecological-environmental activist community and public regulatory agencies have resulted in fewer and fewer pesticide registrations in the United States and, consequently, less related research and development of pesticides. It therefore is of interest to identify and/or develop, "biorational" formulations which have lower animal and environmental toxicities yet are effective in controlling insect and arachnid pests.

Relevant Literature

A method of protecting crops from attack of pests including insects using a composition comprising cinnamic aldehyde and requiring an antioxidant is disclosed in U.S. Pat. No. 4,978,686. Protection of crops against insect pests by applying an aqueous composition containing a cinnamaldehyde is disclosed in French patent application 2529755. U.S. Pat. No. 2,465,854 describes an insecticidal composition containing a cinnamic aldehyde derivative.

U.S. Pat. No. 4,402,950 describes the deactivation of viruses inside living human and animal organisms by application of a terpene obtainable from aromatic plants by steam application. The terpenes cited are: black pepper oil, cinnamon flour oil, cardamon oil, linallyl acetate, cinnamic aldehyde, safrol, carvon and cis/trans citrao. Antifungal-antibacterial detergents containing cinnamic compounds are reported in U.S. Pat. No. 4,477,361.

SUMMARY OF THE INVENTION

The present invention provides a method for protection against attack and infestation by insect and arachnid pest populations using compositions containing as an essential ingredient at least one aromatic aldehydes. The method includes the step of contacting a target pest with an amount of a aromatic aldehyde sufficient to control growth of the target pest. The aldehyde can be provided in a variety of formulations. It also can be provided for target pests as a component of a trap. Optionally the trap contains a chemoattractant for the target pest. The growth modulating product has a formula shown in (1) below.

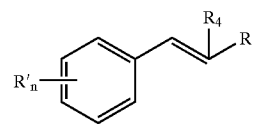

wherein R represents —$CH_2OH$ or —CHO; n is an interger from 0 to 3 and each $R^1$ independently represents —OH or an organic substitutent containing from 1 to 10 carbon atoms and from 0 to 5 heteroatoms, wherein the total number of carbon and heteroatoms in all $R^1$ substitutents of said compound is no more than 15; and $R_4$ represents hydrogen or an organic constituent containing from 1 to 10 carbon atoms. These compounds include naturally occurring compounds, such as cinnamic aldehyde, coniferyl aldehyde, and closely related compounds. Also of interest are alpha substituted aldehydes, such as alpha hexyl cinnamic aldehyde (HCA), and α-butyl cinnamic aldehyde (BCA). The invention finds use in controlling pest populations in areas of infestation, or areas susceptible to infestation and/or killing target pest populations.

BRIEF DESCRIPTION OF SPECIFIC EMBODIMENTS

Methods and compositions are provided for obtaining and/or maintaining an area substantially free of pests such as insects and arachnids using aromatic aldehydes, such as alpha hexyl cinnamic aldehyde and alpha butyl cinnamic aldehyde to biocontrol the area. By "biocontrol" is intended control of pests via direct pesticidal activity on a target pest, including larvae and ova, or by indirect pesticidal activity by antibacterial action on symbiont bacteria resident in the target pest. A target pest colonizing an area is contacted with a natural product. By "colonizing" is intended association of a pest with an area which provides access to organic matter which serves as a source of nutrients for the pest, typically essential nutrients such as amino acids, particularly methionine. By "natural product" is intended an organic compound of natural origin that is unique to one organism, or common to a small number of closely related organisms, and includes secondary metabolites provided by the organic matter. The natural products can be isolated from a natural source, be wholly or partially synthetic, or be produced by recombinant techniques. The amount of natural product that is provided, either applied to organic matter colonized by the target pest or as bait, will depend upon the degree of infestation of the area and to some extent upon the formulation and the specific compounding used and therefore should be empirically determined for particular applications.

The compositions and methods of the subject invention offer several advantages over existing compositions and methods, including that they are safe for use around humans, animals and food sources at the concentrations used. Additionally, the compositions can be used to impregnate organic matter which serves as a nutrient source for a target pest and/or can be provided bound to a solid support which itself is non-toxic to animals, including humans. The formulation residuality also can be managed. This is of benefit when short term residuals are desired for integrated pest management programs with beneficial insects. In addition, the formulations are effective against pests which are resistant to other agents and also are effective on multiple target organisms, including insect targets known to be resistant to conventional treatments. This reduces the need for application of multiple agents for biocontrol of more than one target pest. Reentry time also is not an issue. Typically the formulations are rapidly lethal to a target organism; this is a particularly valuable characteristic when coupled with no reentry time. Another advantage is that the aromatic aldehydes in particular have positive organoleptic and olfactory properties which in some cases may improve the smell of a treated area. The odor of HCA for example is described as floral or jasmine-like with some herbaceous character (Technical Data Sheet).

When applied to animals, including humans, the subject formulations are non-toxic and non-irritating to the skin at the concentrations used. For example, α-hexyl cinnemaldehyde (HCA) has an oral $LD_{50}$ of 3.1 g/kg in rats and a dermal $LD_{50}$ of greater than 3 g/kg (Moreno, O.M. Report to RIFM, Mar. 24, 1971). HCA was found to be moderately irritating when the neat compound was applied to intact or abraded rabbit skin for 24 hours under occlusion (Moreno). When tested at 12% in petrolatum, HCA produced no irritation after a 48 hour closed-patch test on human subjects and produced no sensitization in a maximization test carried out on 25 human subjects (Kligman (1966) *J. Invest. Dermatol.* 47: 393). HCA at 20% in diethylphthalate produced no positive reactions in a repeated insult patch test conducted on 100 human subjects. In studies using the maximization test in guinea pigs, Senma and coworkers report a tendency that as the number of hydrocarbons of alkyl groups replacing the alpha-hydrogen in cinnamaldehyde increased, the rate of sensitization reaction declined.

The subject formulation is as shown in formula (1) above. A preferred formulation is shown in formula (2) below:

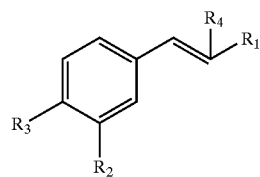

wherein $R_1$ represents —CHO; $R_3$ represents —OH or an organic substitutent containing from 1 to 10 carbon atoms, and $R_2$ represents a methoxy group or an organic substituent containing from 1 to 10 carbon atoms, and $R_4$ represents a hydrogen or an organic substituent containing from 1 to 10 carbon atoms. Of particular interest are aromatic aldehydes. Examples of aromatic aldehydes of use in the present invention are cinnamic aldehyde ((3) below):

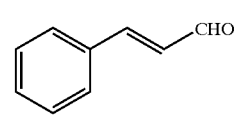

(3)

and coniferyl aldehyde ((4) below).

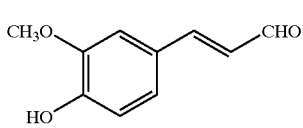

(4)

Other compounds of interest include analogs of the compound of formula (1) such as compounds substituted at the alpha position with an alkyl, such as a hexyl group, a butyl group or a branched alkyl group such as an amyl group. Generally the group at the alpha position is from C-4 to C-10. Such compounds include alpha hexyl cinnamaldehyde, α-butyl cinnamaldehyde and alpha amyl cinnamaldehyde. The chemical structure of alpha-hexylcinnamic aldehyde (HCA) is shown in (5) (below).

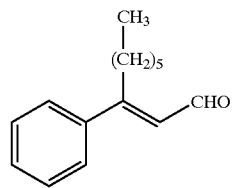

The Chemical Abstracts Service (CAS) name of HCA is 2-(phenylmethylene) octanal and the CAS Registry Number is [101-86-0]. The compound is also described by the chemical name of 2-hexyl-3-phenyl-2-propenal. The compounds's formula is $C_{15}H_{20}O$ and molecular weight is 216.3. HCA can be obtained from Firmenich; their product is composed principally of the (E)-cis isomer (93.8% maximum), and the (Z)-trans isomer (6% maximum). Among minor components is the self aldol condensation product of octanal (1–1.5% (Personal Communication, June Burkhardt, Firmenich, Plainsboro, N.J.).

A number of the aromatic and aliphatic aldehydes which may find use in the subject invention, such as benzaldehyde, acetaldehyde, cinnamaldehyde, piperonal, and vanillin are generally regarded as safe (GRAS) synthetic flavoring agents (21 CFR §172.515). Among these compounds is HCA. HCA was in public use before the 1950's and today is widely used in consumer preparations (soaps, detergents, creams, lotions, perfumes) (Monographs on fragrances raw materials. Food Cosmet. Toxicol. 12: suppl., 915, 1974). HCA was granted GRAS (generally recognized as safe) status by FEMA (Flavoring Extract Manufacturers' Association. Survey of flavoring ingredient usage levels. No. 2569. Fd. Technol., Champaign, 19: (part 2) 155, 1965) in 1965 and is approved by the US FDA for use in food (21CFR121.1164). The Council of Europe (1970) (Council of Europe. Natural and Artificial Flavouring Substances. Partial Agreement in the Social and Public Health Field. Strasbourg, List A(1), Series 1, no. 129, p. 55, 1970) included HCA in the list of admissible artificial flavoring substances at a level of 1 ppm. In addition, surfactants which can be used as emulsifiers for the aromatic compounds, including the Tweens (polysorbates) already are used as food additives, as is saponin (which also has GRAS status).

The aromatic and aliphatic aldehydes of the subject invention are prepared by various synthetic methods known to those skilled in the art. For example, see, J. March, ed., Appendix B, *Advanced Organic Chemistry: Reactions, Mechanisms, and Structure,* 2nd Ed., McGraw-Hill, New York, 1977. Cinnamaldehyde may be prepared synthetically, for example, by oxidation of cinnamyl alcohol (Traynelis et al., *J. Am. Chem. Soc.* (1964) 86:298) or by condensation of styrene with formylmethylaniline (Brit. patent 504,125). The subject aldehydes may also be obtained by isolation from natural sources. For example, cinnamaldehyde may be isolated from woodrotting fungus, *Stereum subpileatum.* Birkinshaw et al., *Biochem. J.* (1957) 66:188.

HCA can be synthesized as described, for example, in U.S. Pat. No. 5,055,621. On a laboratory scale, HCA can be synthesized by reaction of benzaldehyde with octanal under a nitrogen atmosphere (aldol condensation). The reaction is conducted in a stirred flask charged with methanol, 309 ppm diphenylamine, potassium hydroxide and benzaldehyde. Following the slow addition of octanal, the reaction mixture is brought to a pH of 7.5–9.5 with acetic acid. Following evaporation of methanol and wash of the reaction mixture with water, the organic phase is transferred to a distillation unit. Approximately 20–24% of the pot charge is removed as benzaldehyde and "lights", with the remaining distillate constituting alpha-hexylcinnamic aldehyde "heart cut." The "heart cut" is subjected to an additional fractionation, in which 1–5% (by weight) of the material may be removed in "light" fractions, depending upon odor evaluation. The final product is a light yellow oil having a specific gravity of 0.955–0.965 at 20° C., a refractive index of 1.548–1.562 at 20° C., a boiling point of 305° C. at 1 atmosphere, and a melting point of 26° C. The commercial product is stabilized with the addition of 0.04% 2, 6-di-tert-butyl-p-cresol (butylated hydroxytoluene or BHT), which serves as an anti-oxidant (Technical Data Sheet, Hexylcinnamic aldehyde 907600, Revision 853, Firmenich Inc., Plainsboro, N.J.). HCA also can be isolated from rice where it has been reported to occur naturally. (Givaudan-Roure Index, Givaudan-Roure Corporation, Clifton, N.J., 1994, p. 89).

HCA is a low to moderately volatile compound, having a vapor pressure of $70 \times 10^{-5}$ mm Hg at 25° C. Its parent compound, cinnamic aldehyde, has a vapor pressure approximately 40 times higher ($2970 \times 10^{-5}$ mm Hg at 25° C.). For comparison purposes, the insect repellant N,N-diethyl-m-toluamine has a slightly higher vapor pressure ($167 \times 10^{-5}$ mm Hg at 25° C.) (Reifenrath, W. G. (1995) *Volatile Substances. Cosmetics and Toiletries,* 110: 85–93).

An alternative to synthesizing aromatic aldehydes is to prepare them by recombinant means, for example, a microbial host. The resulting microbes are used either to produce the aromatic aldehydes in a fermentation system or as a natural delivery system of the aromatic aldehydes in viable or non-viable microbial preparations. Yeasts, especially *Saachoromyces cerevisiae,* are preferred organisms for this purpose because they have already been engineered for high-level expression of PAL (Faulkener, J. D. B. et al., Gene 143:13020, 1994) and a plant cinnamate 4-hydroxylase has been shown to function in yeast (Urban, et al. 1994 *Eur. J. Biochem* 222:843–850).

The expression of PAL introduces the capability to produce cinnammic acid from phenylalanine. Two additional enzymic steps are required to produce cinnamaldehyde from phenylalanine. In plants, these steps are catalyzed by the enzymes cinnamate:CoA ligase (CL) and cinnamoylCoA reductase (CCoAR) but as 4-coumarateCoA ligase (4CL) can also use cinnamic acid as substance (Knobloch, and Hahlbrock 1977, *Arch. Biochem. Biophys.* 184:237–248, 4CL can be used instead of CL. More than 20 cloned PAL genes and more than 6 4CL genes have been described in sufficient detail (GenBank) to facilitate their use in practicing the current invention. A gene for a CCoAR is obtained from plants by applying standard gene cloning techniques to isolate a cDNA clone using as a probe sequence derived from the amino acid sequence of the N-terminus, or peptide fragments, of the purified protein. CCoAR has been purified and partially characterized from soybean cultures (Wengenmayer et al., (1976) *Eur. J. Biochem,* 65:529–536; Luderitz, and Grisebach, *Eur. J. Biochem,* 119:115–124, 1981), spruce cambial sap (Luderitz, and Grisebach, supra), poplar xylem (Sarni, et al., Eur. J. Biochem, 139:259–265, 1984) and differentiating xylem of *Eucalyptus gunnii* (Goffner, et al., Plant Physiol. 106:625–632, 1994). The preferred method of purification is that of Goffner et al. (supra) because it results in a single protein band on SDS-polyacrylamide gels that an be used for protein sequencing.

The cloned genes are introduced into standard expression vectors and used to transform a microbial host, preferably yeast, by standard transformation techniques such as electroporation (Becker, and Guarante, *Methods in Enzymol,* 194:182–187, 1991). Standard enzyme assays are used to confirm the functional expression of the engineered genes and assays for aromatic aldehydes are used to select strains with maximal production. Because aromatic aldehydes have antimicrobial properties it is preferred to use expression vectors that will cause expression of the introduced genes only late in the growth cycle or in response to a chemical inducer. It may also be desirable to grow the engineered microbial host in an immobilized whole cell reactor (e.g., Evans, et al., *Biotechnology and Bioengineering* 30:1067–1072, 1987) to prevent the aldehydes from accumulating in the culture medium.

In addition to the specific compounds of the formulas (1), (2), (3), (4) and (5) set forth above, derivatives of any of these compounds that produce a compound of the formula identified above upon action of a biological system on a precursor are considered to be equivalent to compounds of the invention. Thus application of precursor compounds to pests which can metabolize the precursors to produce a specific compound identified in the formulas above is equivalent to the practice of the present invention. Biological conversion of precursor compounds into aromatic aldehydes is described in, for example, U.S. Pat. No. 5,149,715 and references cited therein. See also Casey and Dobb *Enzyme Microb. Techol.* (1992) 14: 739–747.

Additional components (other than those of formula (1)) can be added to the formulation to modulate the effect of at least one other compound present in the formulation whereby the combined action is greater than that without the addition of components and preferably is synergistic with the components of formula (1) in the formulation. By synergistic is intended that the activity of the formulation with the additional component as compared to a formulation which does not contain the component is greater than would be expected by adding the effects together.

Preferred additional components include saponins. Saponins are a class of compounds, each consisting of a sapogenin portion and a sugar moiety. The sapogenin may be a steroid or a triterpene and the sugar moiety may be glucose, galactose, a pentose, or a methylpentose. S. Budavari, ed., *The Merck Index,* 11th ed., Merck & Co., Inc., Rahway, N.J. 1990, p. 1328. Saponins for use in the present formulation include sterol glycosides widely distributed in plants, wherein each saponin consists oaf sapogenin and at least one sugar moiety. The sapogenin comprises a steroid or a triterpene and the sugar moiety may comprise glucose, galactose, pentose, or methylpentose. The saponins for use in the present invention can be produced and/or isolated from various plant parts including fruit, leaf, seed and/or root, using means known in the art, from a variety of sources including the various plants known to produce them, ranging from yucca, quillaja, agave, tobacco, licorice, soybean, ginseng and asparagus to aloe woods. Saponins for use in the present invention are preferably non-toxic to humans and higher animals. Most preferably the saponin for use in the present invention is non-toxic food grade, the source being from yucca plants with the most preferred being derived from *Yucca schidigera* or *Y. valida* and their equivalents. Saponins from *Yucca schidigera* contain steroidal saponins with the major sapogenins being sarsapogenin and tigogenin. The sarsaponin yields on hydrolysis, sarsasapogenim (sarsasapogenim 5-beta, 20-betaF, 22-deltaF, 25-betaF; also known as spirostan-3-beta-01 and parigenin), glucose and galactose. The sarasapogenim has a molecular formula of $C_{27}H_{44}O_3$. Nobel, Park S., *Agaves,* Oxford Univ. Press, New York, 1994. Accordingly, derivatives of these compounds which produce a formulation having the desired pest growth controlling properties are considered equivalents of the invention. Saponins have diverse activities which are attributable to the chemical make-up of a particular saponin and most typically are dependent on the source form which the saponin is derived. For example, saponins derived from Japanese Camilla control the growth of mosquito larvae. Saponins from sources other than Yucca plants can be used as active agents in insecticidal compositions. As appropriate, it is preferable to select a saponin that increases the pest growth controlling effect of a formulation as compared to a formulation that excludes the saponin.

The effect of saponin as an additional component in the formulation is determined by the addition of varying amounts of saponin admixed or applied separately in combination with a given formulation of aromatic aldehyde(s). The effect of the formulation is measured by examining the susceptibility of particular pests to each formulation with or without a serial dilutant of saponin. Generally an effective amount of saponin is in the range of about 0.01 to 3% and most preferably about 0.25% v/v aqueous solution of 10° brix saponin extract. 10° brix is a term of art in sugar chemistry. The brix degrees equals the percent by weight of sugar in the solution. Hawley, ed., The Condensed Chemical Dictionary, 10th ed., Van Nostrand Reinhold, New York, 1981, p. 149.

Additional components such as an aqueous preparation of a salt of a polyprotic acid such as sodium bicarbonate, sodium sulfate, sodium phosphate or sodium biphosphate can be included in the formulation, where the addition increases the pesticidal properties of the formulation and/or confers other positive characteristics to the formulation, for example, by rendering it substantive for applications where it is desirable that a residue remain on the surface contacted with the formulation. Generally, the formulations are effective without the use of antioxidants other than the inherent antioxidant properties of particular aldehydes, for example, coniferyl aldehyde.

Stability of the formulation can be evaluated by a variety of methods, including accelerated tests in which a formulation of interest is exposed to elevated temperatures over a set time. Samples of the formulations are taken at regular intervals and analyzed chemically by methods known to those skilled in the art to determine the rate and nature of degradation. For example, HCA can be analyzed by Gas Liquid Chromatography (GLC), using a 30 meter non-polar polydimethylsiloxane capillary column (e.g. HP-1, Hewlett-Packard, or SPB-1, Supelco) and a flame-ionization detector. Using helium as a carrier gas (8 ml/min.) and a column temperature of approximately 240° C., the (E)-cis isomer (major component) has a retention time of approximately 6.0 minutes and the (Z)-trans isomer (minor component) has a retention time of approximately 6.3 minutes.

Of particular interest is the addition of adjuvants to a formulation. By "adjuvant" is intended a substance added to a formulation to aid the operation of the main ingredient. A spray adjuvant performs this function in the application of an agricultural chemical. An effective spray adjuvant may be formulated to contain one or more surfactants, solvents or co-solvents. Systems containing surfactants, water and oily components have many other possibilities of forming ordered phases; the surfactant can organize itself into aggregates of various shapes to create micelles, with a first order phase as one of the possibilities. The surfactant can also collect at the interface between interpenetrating oil and water phases to create a microemulsion. A preferred surfactant for pesticides are the saponins. Saponins may be used as an adjuvant and surfactant and for reducing phytotoxicity. For both phytotoxicity control as well as toxicological safety, preferred saponins are from Yucca spp. Preferred saponins that do not bind cholesterol include those from asparagus.

The compound may be used either alone or in combination with other active or inactive substances and may be applied by spraying, pouring, dipping, in the form of concentrated liquids, solutions, suspensions, powders and the like, containing such concentration of the active compound as is more suited for a particular purpose at hand. Generally, the compositions are prepared in the form of a liquid concentrate to be diluted at the time of use to about 1 g/l to 50 g/l of aromatic aldehyde. The concentrate is typically at least 10×the final diluent, and can be prepared as a 20–40% concentrate, generally 25–5% of aromatic aldehyde. The formulation usually is prepared as two premixed compositions which are contained prior to dilution and use. Thus one premix concentration excipients and a preventative and the second premix can contain the active ingredient, excipients and surfactants. Such a formulation is shown in the Table below.

TABLE

| Ingredients: | lbs. | gal. |
|---|---|---|
| 30% Cinnanic Aldehyde Concentrate | | |
| Premix A | | |
| Water, deionized | 3793 | 455 |
| Gelwhite GP | 97 | 5 |
| Glycerine | 258 | 24 |
| Kalzan S | 12 | 3 |
| Dowicide A | 3 | 0 |
| Total | 4164 lbs. | 486 gal. |
| Premix B | | |
| Cinnaldehyde Tech. 9% | 2526 | 290 |
| Emersol 2301 Stearic Acid | 1160 | 166 |
| Tween 80 | 514 | 58 |
| Total | 4200 lbs. | 514 gal. |
| Cinnacure 30% Flowable | | |
| Premix A | 4164 | 486 |
| Premix B | 4200 | 514 |
| Total | 8364 lbs | 1000 gal. |

The formulation may be applied, for example, in the form of dilute solution, in a suitable solvents directly to an area of pest infestation or an area susceptible to infestation. Carriers which can be used include conventional nontoxic excipients such as glucose, starch, aluminum hydroxide and the like. Carriers for topical administration can be solid-based dry materials well known in the art for the formulations in the powdered form, and can be liquid or gel-based materials for formulations in liquid or gel forms depending upon the method of application. Typical carriers for dry formulations include dextrose, fructooligosaccharides, xanthan gum, mannitol, lactose, starch, magnesium stearate, sodium saccharin, talcum, cellulose, glucose, sucrose, magnesium carbonate, glycerin, glucooligosaccharides, inositolmaltodextrin, magnesium stearate, micro-crystalline cellulose, sucrose, talc, trehalose, and the like. Typical liquid or gel-based carriers are water and physiological salt solutions, alcohols and glycols (such as butanol, cetylstearyl, ethanol, ethylene glycol, methanol, propanol, and propylene glycol), white petrolatum, isopropyl myristate, lanolin, mineral oil, fragrant oil, nasturtium extract oil, hydroxypropyl cellulose and the like. Numerous other components such as dyes and dispersing agents can be included in the composition. As an example, for use as a means of cleansing a surface, such as a carpet, pet bedding, pet fur, clothing, skin, and the like, although the aldehyde can be formulated alone as an aqueous solution, it also can be prepared as a soap or a detergent. Detergents which can be used include anionic detergents such as those described in U.S. Pat. No. 4,978,686. For some applications the compound(s) are bound to a solid support for application in powder form or in a "trap". As an example, for applications where the formulation is to be used as a trap or as bait for a particular pest, the formulations of the subject invention can be sprayed directly in an area of infestation or they can be bound to a solid support or encapsulated in a time release material. Where a solid carrier is used, materials which can lead to oxidation of the active aldehydes should be avoided. Examples of delivery systems include starch-dextran, and the like. See Yuan et al., *Fundamental and Applied Toxicology* (1993) 20: 83–87 for examples of delivery systems.

The target pests include insects and arachnids, particularly those which colonize organic matter, more particularly those insects and arachnids that colonize organic matter which is an elicitor for the pest. By elicitor is intended that the organic matter provides nutrients required by the pest. Also of interest as target pests, and the organic matter or habitat which provides their nutrients, are as follows. Flies, (*Muscara domestica* (L.) and *Stomoxys calcitranus* (L.), decaying organic matter, particularly matter which includes putrescine; fleas Aphaniptera (Siphonaptera), blood ticks *Argas* (Persicargas) *arboreus* (Ixodoidea:Argasidae), hard ticks (family Ixodidae), soft tick (family Argasidae), blood; Dictyoptera: Blattellidae, decaying organic matter; termites Isoptera: Rhinotermitidae, organic matter, particularly matter containing cellulose; ants (*formicidae*) including fire ants *Solenopsis invicta*), carpenter ants (*Camponotus pennsylvanicus*), army ants (Eciton); mosquitos (*Aedes aegypti*), blood. Also of interest is *Boophillus annulatus*, the hard tick associated with severe cattle problems in Australia and elsewhere and with mice. Generally, lice are divided into two orders, the Anoplura (sucking lice) and the Mallophaga (all others, e.g., elephant lice and chewing lice).

Also of interest as target pests are mites, such as spider mites (Arthropoda), dust mites, mites which infect honey bees, and a variety of other mites, including those of the following orders: Cryptostygmata (beetlemite); Mesostigmata (red mite of poultry); Prostigmata (gall mite, water mite, chiggers and reg bug (follicle mite, quill mites); Astigmata (flour mite, furniture mite, fur mite, scabies or itch mite, fuschia mite and dust mite). It is a theory of the invention that many of the insects and arachnids which are susceptible to treatment with the subject formulations are those which harbor symbiotic bacteria in their gut. Accordingly, insects and arachnids other than those listed which harbor symbiotic organisms can also be controlled with the subject formulations.

In use, a formulation containing the pesticide is introduced to an area of infestation. For example, the formulation is sprayed on as a wet or dry formulation on the surface of organic material infested with a target pest, or organic material susceptible to infestation with a target pest. Alternately, the formulation can be applied wet or dry to an area of infestation where it can contact the target pest.

In some instances, time-release formulations may find use, particularly for applications to animals, or areas which are subject to reinfestation, such as animal quarters. When used in a solid form or microencapsulated, the dosage used would typically be on the order of 1% to 35% on a w/w basis, the maximum loading to be determined as a function of shell material selected. Analytical chemical techniques are used to determine and optimize rate of release. For qualitative purposes, GC techniques can be used to determine the amount of aldehyde released. The samples of encapsulated (pelletized) product are sampled at different time periods to measure release. Alternatively, volatile gases released from the formulation can also be analyzed. For measuring the activity of spray or powder applications the stability of the formulations over time can also be evaluated by the GC methodology using techniques known to those skilled in the art. Methanol or alcohol extractions of the formulations also can be prepared and evaluated by HPLC analysis.

The aldehyde components can be coupled to a solid support, optionally through a linker such as a polysaccharidase binding domain, where the solid support is a polysaccharide such as cellulose, particularly microcrystalline cellulose. The preparation of cellulose binding domains is described in U.S. Pat. Nos. 5,340,731; 5,202,247 and 5,166,317 and PCT application no. WO 94/24158. The aldehydes can be coupled to the binding domains, with or without a cleavable bond, using methods well known to those skilled in the art. These formulations can be used to directly impregnate a surface comprising the appropriate polysaccharide, for example where the surface is a cellulose, such as paper or wood, a cellulase binding domain is used. As an example, the aromatic aldehyde-cellulase binding domain composition can be used to impregnate wood which is subject to or already infested with termites. In other applications, the aldehyde-cellulase binding domain composition can be bound to paper as a trap or to microcrystalline cellulose wherein the granules can be transported back to the colony. Optionally, the bait or trap additionally can include a chemoattractant for the target pest, such as putrescine for flies or cadaverine for cockroaches bound to the cellulose support via a cellulase binding domain. Other examples of chemoattractants are well known to those skilled in the art.

In addition to providing bait or traps, infestations of target pests also can be treated using powder or detergent formulations, for example as a carpet shampoo to treat infestations of dust mites and fleas and other susceptible pests. The formulations of the subject invention generally are non-staining and additionally often impart a pleasant odor to the treated surface. The formulations also can be used as emulsions or gels for treatment of infestations of animals or humans, including infestations with fleas and ticks. Generally, the formulations are safe for ingestion at the concentrations used and additionally, typically have positive organoleptic and olfactory characteristics.

In order to determine the susceptibility of particular pests to the subject compositions, in vitro and in vivo tests such as are described in the Examples can be used. As appropriate, the formulations also need to be evaluated for dermatological effects; it therefore is important where appropriate that at least one evaluation of the toxicity of the formulations be tested on animal hosts for the target pest or on animals which may come in contact with a treated surface so that the dermatological effects can be tested for the dosage of pesticide used. Such dermatological sensitivity tests can be conducted using methods known to those skilled in the art. In some instances it may be necessary to adjust the treatment formulation so as to reduce any dermatological effects associated with the formulation.

The method of the present invention is carried out by introducing into a target pest a sufficient amount of a pesticide to impair growth and/or viability of the target pest and thereby decrease the population of that pest in an area. The method of introduction of the subject pesticide into the target pest can be by direct ingestion by the target pest from a trap, or by feeding of a target pest on nutrient-providing organic matter treated with the pesticide. In some instances, the pesticide may be absorbed by the pest, particularly where the formulation provides for uptake by the outer tissues of the pest, particularly a larval or other pre-adult form of the pest, such as a detergent formulation. In some instances, the exoskeleton of the target pest is substantially dissolved by contact with the formulation. For some applications, it may be necessary to deliver the formulation to the location of the pest colony.

The method of use of the formulations will depend at least in part upon the pest to be treated and its feeding habits, as well as breeding and nesting habits but generally is in the form of spraying, dusting or washing an area of infestation with the subject formulations. The following are examples of infestations of particular types of pests that can be so treated. For spider mites and relatives (as exemplified by the two spotted spider mite (*Tetranychus urticae*)), life stages include the egg, an early, six-legged immature stage, and eight-legged immature stage and the adult stage. With ambient and warm temperatures and low humidity, the generations are complete in as little as ten days. Adult females typically lay up to five eggs per day over the course of 14 to 21 days. The adult arachnid pierces plant cells and feeds on the sap. There may appear small white flecking injuries surrounding the feeding mites, and generalized discoloration occurs, with bronzing as infestations progress. Vigor is reduced and premature leaf drop may occur. Raspberry, rose, bean, cucumber and marigold are among the most commonly and seriously damaged. Moreover, the two spotted spider mite is also the most common species that damages greenhouse crops and interim plants. Spider mites are extremely difficult to control with pesticides, and many commonly used pesticides (e.g., Sevin) can increase problems by destroying natural predators. Miticides such as malathion and orthene are often ineffective because spider mites have developed resistance to them.

Ticks are the largest group of the subclass *Acari* and are obligate blood-sucking ectoparasites of land vertebrates. Certain species are pests of domestic livestock, while another group transmits human disease. Ticks are classified into three families, all but one species belonging to the Ixodidae (hard ticks) for to the Argasidae (soft ticks). Hard ticks get their name from the thickened shield (scutum) on top of the front of the body. They possess prominent well developed mouthparts, needed to secure themselves to their roving hosts during feeding, which can take several days. A common hard tick is the cosmopolitan brown dog tick. The compounds of the invention can be applied to the host as sprays, powder, dusts, shampoo and dips and can also be used to treat animal collars or bedding. Soft ticks lack a scutum and have relatively weak mouthparts, positioned inconspicuously on the underside. Soft ticks are habitat ticks: they remain in the host's retreat and feed when it returns. Their mouthparts are not exceptionally well-armed, as the host is generally at rest while feeding proceeds. After feeding, ticks usually fall to the ground to lay eggs or molt. Compounds of the invention can be used to treat nests and abodes, paddocks, pens, and the like, by spraying with an effective amount.

Several species of ants (*Formicidae*) can be a nuisance in the garden, and inside the home, especially the kitchen area. Most species of ants in the United States are social insects that live in colonies or nests, in which remain the egg-laying queens, the young or larva, pupae and many worker ants. The workers, all sterile females, care for the colony as well as search for food and bring it to the nest. In the spring or fall, ant colonies may produce winged males which fly about, mate, and have the ability to start a new colony. Baits can be formulated which the ant will carry back to the nest. Ants construct mounds or small hills of granulated soil which may smother surrounding vegetation. Grass may also be killed as the soil around the grass roots dries out from the effects of the digging and burrowing. Some species of ants which frequent turfgrass areas, and eventually construct anthills, include the little black ant (*Monomorium minimum*), the pavement ant (*Tetramorium caespitum*), and the thief ant *Solenopsis molesta*). Compounds of the invention can be used to treat nests and anthills, as well as those areas in which they are likely to form, by treating with an effective amount. Other ants may be in planted areas or near grass areas. The black carpenter ant (*Camponotus pennsylvanicus*) nests in dead trees, logs and even structural wood in houses. These large, winged, black ants often exceed 1 mm in length. Winged males and females may swarm occasionally. Baits and contact sprays can be used in eradication. The red imported fire ant (*Solenopsis invicta*) colony constructs honeycomb mounds containing up to $0.5 \times 10^6$ worker ants. These mounds are found in pastures, roadsides, field borders, and in home lawns. The ants build mounds in many areas but prefer sunny sites and clay soils over sandy soils. Fire ants increase their mound size in wet seasons to move above the moist areas. Soils used in nest and mound construction could be treated with a concentration of formulation to kill workers and soldiers and reduce mound size.

Mosquitoes undergo a complete metamorphosis during their life cycle. Water breeding-eggs need $H_2O$ to hatch (some species lay eggs on dry ground, others in water directly). Larvae are fast growing and shed skin four times in four to ten days. They feed on one-celled organisms and each other. Pupae do not eat and become adults in two to four days. Formulations of compounds of the invention can be used to treat environments that encourage accumulation of standing water (for example, stagnant ponds, discarded tires, pots, cans, and the like). In waterfowl areas (wetlands ponds, lakes, and the like), the concentration of formulations of compounds of interest can be adjusted to kill late stage larvae. Prolonging larvae life may provide waterfowl food since some species are reported to eat mosquito larvae (e.g., ducks). Adults can be controlled by spray contact insecticide containing an effective concentration of the subject compounds on surfaces or in flight.

Cockroaches undergo a gradual metamorphosis during their life cycle. Many oviparous-eggs deposited with glandular secretions, harden to form a tough protective capsule-ootheca, which sticks to substrate (usually concealed by debris) or carried on end of female's abdomen. Direct contact spray of nymphs and adults when possible can be used to control the insects or spraying of traffic areas (e.g., food prep areas, refuse areas, and the like) with an effective amount. Alternatively, encapsulation of formulations of the compounds of interest in a chemoattractant shell can be placed in a trap or high traffic surface area.

Flies undergo a complete metamorphosis. Eggs are deposited in a moist habitat since legless larvae require moisture. Parasitic flies are abundant in many environments and lay eggs in or on a vast range of animals, other insects, and vertebrates. Larvae are active predators of insects for flower visitors. Flies can be killed at the adult stage with an effective amount of the compounds of the subject invention formulated as a contact insecticide (for example, as a spray, a trap with sticky paper, other types of traps, and on solid bait).

Fleas undergo a complete metamorphosis. Larvae are free living and legless with a developed head. Fleas are mammalian parasites and favor hosts that build nests, burrows, and dens. Larvae feed on host blood that has dried and passed out of adult flea as feces while host is in its lair. Larvae are vulnerable to climatic change (desiccate in dry conditions and drown in a droplet of water). This limits fleas to certain environments (nests, dens and so on.) Eggs, larvae and pupae (silk cocoon) develop freely in the nest or habitat of host (e.g., fur fleas of feline and canine mostly in nests (beds). In addition, fleas commonly infest dogs and cats and many have experienced the painful irritating bites that result when they suck the blood of humans. Fleas bite mostly above the legs and it is rather characteristic that there are frequently two or three bites in a row. Fleas shift from host to host and feed indifferently on several kinds of animals. The cat flea (*Ctenocepalides felis* Bouché order Siphonaptera, family Pulicidae) is nearly as likely to be found on a dog or a human as on a cat. The subject compounds can be used to control fleas by contacting a host or its habitat with an effective amount of a formulation containing the subject compounds as a spray, dust, powder or encapsulated in an indigestible material suitable for passage through the digestive system of rumen and monogastric mammals.

Termites undergo metamorphosis from eggs to larvae (nymph) to adults with no pupal stage. Nymphs may resemble the adult termite. Termites live in colonies for most life cycle stages. In the lower gut of adults, protozoa pass from adults to the young in via fecal contact. Higher termites have gut bacteria that are involved in the supply of amino acids. Termites can be treated with compounds of the subject invention by directly spraying an appropriate formulation on nymphs and adults. Wood surfaces with which termites come in contact can also be treated with an effective amount of a formulation. Termites can be brought into contact with microencapsulated formulations of the subject invention, and the subject compounds can also be bound to wood surfaces through the cellulose binding domain. Traps baited with attractants and the compounds of the subject invention can be used.

The cotton or melon aphid (*Aphis gossypii* Glover) fly to cotton plants almost as soon as cotton has put out leaves. These small, soft-bodied, pale-green plant lice fly to the plants and start to reproduce. In cool, wet season, when their natural enemies cannot work against them so well, they may become abundant enough to stunt and deform the plants. Often, when the hot weather or summer arrives, they practically disappear. The most important species, feeding above ground, is the cotton or melon aphid *Aphis gossypii* Glover. The subject compounds can be used to control aphids by contacting an aphid or its habitat with an effective amount of a formulation containing the subject compounds as a spray, dust, powder or encapsulated in an indigestible material.

Venomous spiders cause illnesses in mammals ranging from mild local inflammation to a severe systemic reaction. The most venomous spider in North America, the Black Widow *Latrodectus mactans* (Fabricius) and *L. geometricus* (Fabricius) are responsible for human mortality on the order of 0.2%. The other intensely venomous spider found in North America is the Brown Recluse spider *Laxosceles reclusa* (Gertsch and Malaik). Both males and females bite. Compounds of the invention can be used to treat nests and abodes and the like, by spraying with an effective amount.

Scab mite (or Psoroptic Scab)(*Psoroptes equi* (Raispail) and *P. ovis* (Hering)) such as cattle scab mite is a minute whitish eight-legged mite that cause animal injuries by puncturing the skin with their sharp mouth styles. Early symptoms are small reddened pimples that ooze pus. As the mites increase in number, larger areas become covered with yellowish crusts filled with serum. Larger scabs form on the skin over the mites and the hair comes out in great patches. Cattle scabies is a quarantinable disease. Compounds of the invention can be used to control scab mites by contacting the host or its habitat with an effective amount of a formulation containing the subject compounds as a spray, dust or powder and the like.

The common bed bug (*Cimex lectularis*) and its close relatives (poultry bug (*Haematosiphon inodorus* (Duges), the European pigeon bug (*Cimex columbarius Jerjus*), and the swallow bug (*Oeciains vicarius Hrovath*), are frequently pests in poultry houses. At night the nymphs and adults find their way on the sleeping hens and suck their blood. Sitting hens may suffer especially from these pests and may be driven to leave the nests. The bed bug will also attack humans, rabbits, guinea pigs, horses and cattle. On humans the bites become increasingly painful for a week or more. Bed bugs thrive under crowded and squalid conditions. The subject compounds can be used to bed bugs by contacting a host or its habitat with an effective amount of a formulation containing the subject compounds as a spray, dust, or powder, for example.

Mealybugs, aside from strange appearance, are not too different than aphids, psyllids, and phylloxera. They suck the juices from plants and spread disease. The honeydew they excrete invites the growth of a sooty fungus which interferes with photosynthesis of the host plant. The compounds of the subject invention can be used to control mealybugs by contacting a mealy bug or its habitat with an effective amount of a formulation containing the subject compounds as a spray, dust, powder or encapsulated in a digestible material.

The following examples are offered by way of illustration and not by way of limitation.

EXAMPLES

Materials and Methods

The chemicals used in the examples given below were obtained from the following sources: cinnamic aldehyde, Spectrum Chemical Company, N.J.; coniferyl aldehyde, APIN Chemical, U.K.; Tween 80 and sodium bicarbonate Spectrum Chemical Company, Gardena, Calif., alpha hexyl cinnamic aldehyde, Firmenich Chemical Manufacturing Center, Port Newark, N.J. Concentrations are given as the concentration of the indicated solution before dilution.

Example 1

Effect of Formulation on Spider Mite

Activity of cinnamic aldehyde and/or coniferyl aldehyde against two-spotted spider mite, Tetranychus urticae is determined as follows. In a double blind experiment, intersurfaces of petri dishes (60 mm diameter) were treated with 100 µl of a test formulation and allowed to air dry and used within the hour. Twenty adult spider mites were put in each dish and the percent of mortality of the spider mites after 24 hours in contact with the treated dishes Was determined.

TABLE 1

Spider Mite

| Formulation[1] | Percent Mortality (24 hours) |
|---|---|
| CNMA ppm | |
| 25,000 | 99.2 |
| 12,500 | 98.6 |
| 5,000 | 66.4 |
| 2,500 | 78.0 |
| 100 | 56.0 |
| 10 | 51.7 |
| Control | |
| HPLC H$_2$O | 16.2 |
| Vehicle[2] | 49 |
| +Control[3] | 100 |
| Neg. Control (H$_2$O) | 12.6 |

[1]L Cinnamic aldehyde at the indicated concentration in 2% Tween 80, 6% NaHCO$_3$.
[2]2% Tween 80, 6% NaHCO$_3$.
[3]Sevin 10 ppm.

after three hours in contact with a treated plate, is compared to that of spider mites in petri dishes treated only with water.

Plant Foliar Bioassay

Cotton plants are grown in 7.5 mm pot in potting soil in greenhouse. When plants reach 3 leaf stage, they are infested with 60 adult spider mites (6 replications). The mite is allowed to settle and feed. The plant is sprayed to runoff (about 5 ml) with a formulation containing 100 to 2000 pm, (0.1 to 2 g/l) concentration of a test formulation. The plant is covered with a tall plastic cage (5 mm tall×10 mm diameter). The mortality of the spider mites on the plants sprayed with a test formulation is determined and compared with that of spider mites on plants sprayed only with water.

Example 2

Effect of Formulation on Flies

In an air conditioned case measuring 1.5 m×1.5 m×1.5 m, 150 flies (Musca domestica (l..) and Stomoxys calcitranus (l..) are released and sprayed with 8 ml of test product. The test product contains 100 to 2000 ppm of cinnamic aldehyde and/or coniferyl aldehyde in an appropriate formulation. After 15 minutes exposure, the number of flies that are unable to fly are noted. All flies are transferred to a holding case with fresh air and allowed to recuperate for 20 hours. The number of dead flies are counted, and the percentage of flies killed with each formulation compared to that of no treatment and treatment with a formulation known to kill files at a level of about 70%.

Example 3

Effect of Formulation on Fleas

Petri Dish Bioassay

Aphanptera (Siphonaptera) susceptibility is tested as follows. Petri dishes (60 mm diameter) are treated with a specific dose of product (100 to 2000 ppm) dissolved with water, and allowed to dry. Twenty specimens of the insect and twenty larvae of the insect each are put in separate dishes (replicate 10 times). The mortality of insect and larvae after thirty hours in contact with a treated plate is compared to that of insects and larvae treated only with the diluent, and treatment with a formulation known to kill fleas at a level of about 70%.

Contact Treatment

The treatment of cat flea (Ctenocepalides felis) with various formulations containing alpha hexyl cinnamaldehyde is tested as follows. In a double blind experiment, variable concentrations of the formulae were tested for activity against cat flea (Ctenocepalides felis). The initial experiments tested alpha hexyl cinnamaldehyde at concentrations of 5%, 10% and 20% in 6% Tween 80. As controls, a formula blank containing 6% Tween 80 and negative control with no formulae were tested. Fleas were put in direct contact with the formulae and mortality was assessed both visually and by probing at 72 hours after contact.

Approximately 11,356 ml of each formula concentration was sprayed on 0.279 square meter carpet section (DuPont) at 20 PSI. After allowing to air dry (20 minutes), four plugs each 14 cm in diameter were cut from each treated carpet section. One plug was used for each replicate for four total replications. For each treatment and replicate, 25 fleas were introduced on each plug. Plugs were then rolled and put in an escape proof, ventilated 2 liter container. After 72 hours mortality was assessed.

All treatments using concentrations of alpha hexyl cinnamaldehyde yielded greater than 80% flea mortality. Fourteen percent mortality was observed with the 6% formula blank. See Table 2.

TABLE 2

Cat Flea

| Formulation | Percent Mortality |
| --- | --- |
| AHCNMA (%)* | |
| 5 | 84 |
| 10 | 92 |
| 20 | 86 |
| Control | |
| 6% Tween 80 | 6 |
| No spray | 3 |

*AHCNMA = alpha hexyl cinnamaldehyde (% wt/vol) in a vehicle of 6% Tween 80.

Example 4

Effect of Formulation on Ticks

In a double blind experiment, filter papers (90 mm) (Whatman) were treated to uniform saturation with 1 ml of test formula and placed in 90 mm petri dishes. Ten arachnids were placed in each petri dish and the dish closed. Observations of mortality were made at 30 minutes, 1 hour, 3 hours, 6 hours, 12 hours and 24 hours. The cinnamic aldehyde concentrations varied from 10–50,000 ppm in a vehicle of 2% Tween 80, 6% $NaHCO_3$. The effect of vehicle alone or $H_2O$ (HPLC) was also tested. In separate experiments, the effects of the components of the vehicle were evaluated in comparison to water.

In preliminary experiments with the hard ticks (*Ixodea pacificus* and *Dermacentor albipietus*), 100% mortality was achieved in 24 hours, at a concentration of 2500 ppm in vehicle. At concentrations below 2500 in vehicle, there was no effect on mortality. No effect was observed with $H_2O$ or vehicle alone.

In preliminary experiments with the soft tick (*Ornithodoros coriaceus*), 100% mortality was achieved at concentrations below 12,500 ppm in vehicle (Trial 1); and at a concentration of 12,500 ppm in vehicle (Trial 2). No effect was observed with $H_2O$ or vehicle alone. See Table 3.

TABLE 3

*Ornithodoros coriaceus* (Soft Ticks)

| | Number Dead | | |
| --- | --- | --- | --- |
| Formulation[1] CNMA (ppm) | 24 Hours (#/30) | 120 Hours (#/30) | 120 Hours (#/10) |
| 50,000 | NT[3] | NT | 10/10 |
| 45,000 | NT | NT | 10/10 |
| 40,000 | NT | NT | 10/10 |
| 35,000 | NT | NT | 10/10 |
| 30,000 | NT | NT | 10/10 |
| 25,000 | 7/30 | 21/30 | 10/10 |
| 12,500 | 5/30 | 6/30 | 10/10 |
| 5,000 | 3/30 | 6/30 | NT |
| 2,500 | 2/30 | 6/30 | NT |
| 100 | 0 | 0 | NT |
| 10 | 0 | 0 | NT |
| Controls | | | |
| HPLC $H_2O$ | 0 | 0 | 0 |
| Vehicle[2] | 0 | 0 | 0 |

[1]Formulation is the indicated amount (ppm) of cinnamic aldehyde in a vehicle of 2% Tween 80 and 6% $NaHCO_3$.
[2]Vehicle of 2% Tween 80 and 6% $NaHCO_3$.
[3]Not tested.

Example 5

Effect of Formulation on German Cockroaches

Adult male cockroaches (Dictyoptera; Blattelidae) were used to evaluate insecticidal activity of cinnamic aldehyde and/or coniferyl aldehyde by a topical application method.
Topical Application Bioassay Twenty cockroaches were placed in stainless steel pails (20 liter) with lids. After one week provisioned with food, water and harborage, they were sprayed with 5 ml of a test formulation at arm's length (approximately 1 meter) using a Gilmour spray bottle. The number of dead or moribund cockroaches at 5 minutes, 30 minutes, 1 hour and 12 hours after treatment was counted and compared to those untreated (diluent only). Raid (active ingredients: permethrin, pyrethrins and PBO) was used as a positive control. Within five minutes, all cockroaches treated with 2% cinnamic aldehyde (20,000 ppm) in aqueous vehicle (2% Tween 80, 6% $NaHCO_3$) were dead, as were all those treated with Raid. Ten percent of those treated with vehicle alone were dead in 30 minutes, with no further increase in mortality up to 12 hours.

Example 6

Treatment of Western Subterranean Termites (Isoptera: Rhinotermitidae) Laboratory Bioassay
Tray Bioassay Sterilized play sand is treated with aqueous emulsions of each formula and component to provide 500 ppm deposits (wt./wt. sand). 500 g samples of sand are evenly spread ≦1 mm thick over a metal tray (50 by 30 cm). and sprayed with 65 ml of emulsion with an air brush at 1,970 $g/cm^2$ (28 psi) to obtain uniform treatments. Six examples for each formulae and component are prepared. The treated sand is dried in a fume hood for 30 minutes and the insecticidal activity of each formula treated sand is determined by continuously confining termites to treated deposits for 24 h. Ten termites are exposed on 2.5 ml of treated sand in petri dishes (35 by 10 mm) in each of five replicates. Termites and petri dishes are held in a chamber maintained at 93% RH with a saturated sodium sulfate solution. The number of dead or moribund termites after 24 h exposure is determined. Termites are considered dead if unable to right themselves within 5 min. The effectiveness of the test formulation is compared to termites treated with diluent only or with a formulation known to kill termites at a level of about 70%.

Example 7

Effect of Formulation on Ants

The effect of cinnamic aldehyde on adult carpenter ants (*Camponotus pennsylvanicus*) was evaluated as follows.

Twenty adult ants were placed in a 20 liter stainless steel pail with lid. The test formulations were prepared and used within one hour and were shaken immediately before spraying the insects. 8 ml of test solution was sprayed with a fine spray (Gilmour hand sprayer). The insects were observed at 0.5, 1, 8 and 24 hours. Cinnamic aldehyde (2%, 20,000 ppm) in 2% Tween 80 and 6% $NaHCO_3$ in water gave 100% mortality at all time points. Vehicle in 2% Tween 80 and 6% $NaHCO_3$. Raid (active ingredients: permethrin, pyrethrins and PBO) was used as a positive control and gave 90% mortality at 0.5 hr with 100% mortality at all other time points.

Example 8

Effect of Formulation on Mosquitos

Adults

The toxicity of the formulation for mosquitos was determined using adult *Aedes aegypti* mosquitos from the University of California Mosquito Control Research Laboratory at the Kearney Agricultural Center. The experiments were performed as double blind studies.

One ml test formulation was pipetted onto 11 cm #2 Whatman filter paper circle cut to fit shell vials (84 mm×23 mm) which was air dried at room temperature for two hours and placed in a shell vial (84 mm×23 mm). Twenty unblooded adult female mosquitos approximately four days of age were aspirated using gentle suction into each shell vial. The open end of the vial was covered with 1 mm nylon mesh and filter paper cut to fit for complete coverage from an 11 cm #2 Whatman filter paper circle. The vials were placed in a polyethylene mosquito bag (46 cm×20 cm) with a wet paper towel inside and loosely sealed. The bag was gently inflated by gently blowing in air and placed in an incubator at 22° C. for 24 hours with a day light cycle (14 hrs light; 10 hrs dark). Untreated paper and paper treated with $H_2O$ were used as controls. Mortality was determined by counting the number of dead mosquitos.

The efficacy of various concentrations of cinnamic aldehyde in a formulation of 2% Tween 80, 6% $NaHCO_3$ was tested, using concentrations of cinnamic aldehyde ranging from 25,000 ppm to 10 ppm with and without the addition of saponin, 1:60 dilution of a 10° Brix solution. At concentrations down to 100 ppm added to the filter paper, 100% of the mosquitos were killed. At 10 ppm added to the filer paper, 78% of the mosquitos were killed in the absence of saponin, but only 5% with saponin 14% of mosquitos were killed with the addition of 2% Tween 80 and 6% $NaHCO_3$ alone to the filter paper and 50% with the further addition of a 1:60 dilution 10° Brix saponin. The percent mortality is the average of three replications, with corrections for control mortality. See Table 4. Malathion was used as a positive control.

Larvae

Larvicidal activity of test formulations at varying concentrations was tested in a double blind bioassay on larvae of *Culex quinquefasciatus* mosquito. Twenty-five late 3rd-instar larvae of *Culex quinquefasciatus* were placed in 100×80 mm Purex #3250 glass containers. 250 ml distilled $H_2O$ was pipetted into the containers. One ml of test formulation containing 10 to 25,000 ppm cinnamic aldehyde in vehicle (2% by volume Tween 80 and 6% sodium bicarbonate in distilled $H_2O$) was pipetted into each container. A control blank using 1 ml distilled $H_2O$ instead of a test formulation was also prepared.

TABLE 4

Mosquito Adulticide

| Formulation | Percent Mortality | |
| --- | --- | --- |
| (ppm) | CNMA (PGXL) | CNMA + SAP |
| 25,000 | 100 | 100 |
| 12,500 | 100 | 100 |
| 5,000 | 100 | 100 |
| 2,500 | 95 | 100 |
| 100 | 100 | 100 |
| 10 | 78 | 5 |

% are averages of 3 replications with corrections for control mortality

| Control | Percent Mortality |
| --- | --- |
| -Control[1] | 0 |
| -Control[2] | 0 |
| Form Blank | 14 |
| FBI + SAP | 50 |

[1]Plain paper.
[2]$H_2O$.

All treated and untreated glass containers were placed in temperature controlled room at 29° C. Each container was evaluated for larvae mortality at 24 hour intervals. The number of dead larvae were reported. See Table 5 for results of the bioassay. Concentrations above 5,000 ppm cinnamic aldehyde gave 90% mortality at 24 and 48 hours.

TABLE 5

Larvae (*Culex quinquefasciatus*)

| | Percent Mortality (time) | |
| --- | --- | --- |
| Treatment (ppm) | 24 hours | 48 hours |
| 10 | 0 | 0 |
| 100 | 2 | 2 |
| 2,500 | 4 | 4 |
| 5,000 | 8 | 20 |
| 12,500 | 90 | 90 |
| 25,000 | 100 | 100 |
| $H_2O$ Control | 0 | 0 |

Example 9

Treatment of Lice

Determination of Toxicity

Fifty ml of test formula containing various concentrations of cinnamic aldehyde in vehicle (2% by volume Tween 80 and 6% sodium bicarbonate in distilled $H_2O$) is applied as evenly as possible to one half of a filter paper disc (5.5 am in diameter). Two test papers are prepared for each solution. Papers are air dried in a flow of moving air for 30 minutes. Each paper is placed in center of 10 cm glass Petri dish. Ten young adult female lice (5–7 hours after engorgement) are placed in center of the disc and the Petri dish covered. Dishes are placed in an incubator at 30±2° C. and approximately 50% humidity.

After 5 minutes, which allows time for the lice to deaggregate and distribute randomly, the lice on the treated side are counted. Dishes are re-examined after each of a further 4 incubation periods of 2 minutes. Any lice found off the filter paper are excluded from the total sample number and are placed back in the filter paper to be counted on the next inspection. Five replications are undertaken on the same day. Scores are summed, as are the total number of lice sampled, and control checked for random distribution. Repellency is calculated using Schneck (1977) formula.

Determination of Effect of Cinnamic Aldehyde on Choice of Egg-laying Site 9 cm diameter filter paper circles, torn into a square and bisected into two triangles by line (pencil). Paper filter torn as rough edges are attractive egg laying sites. On one half of the filter paper is wetted 200 μl of $H_2O$ or formula and dried for 30 minutes. A batch of 20 young adult female and 20 young adult males are incubated at 30±20° C. over a 24 hour period. Eggs laid are counted. Tests are repeated over 5 days and egg counts summed for each type of area.

Example 10

Effect of α-Butyl Cinnamic Aldehyde on Adult Lice

Adult human lice (*Pediculus humanus*) were treated with α-butyl cinnamic aldehyde to determine its pediculicidal activity. Procedures did not deviate from ASTM B 938-83 (Reapproved 1988), *Standard Test Method for Effectiveness of Liquid, Gel, or Cream Insecticides Against Adult Human Lice*, which is incorporated herein by reference. For each of four replicates, 25 mixed sex lice were placed in a 9 dram plastic vial and covered with a screened plunger to keep the lice from floating to the surface. The vial containing the lice was dipped into a 100 ml beaker containing 2% α-butyl cinnamic aldehyde, which was dissolved in water or distilled water as a negative control. Lice were submerged in the 2% α-butyl cinnamic aldehyde for 1, 4 or 10 minutes. After this time, the test container was removed from the treatment, submerged in a 1000 mL beaker containing distilled water (32° C.) from a wash bottle. Subsequently, lice were allowed to recover in an incubator maintained at 31.7° C. in 60% RH (relative humidity) for 1 hour. Following the recovery period, lice were examined for their ability to move toward heat. For this observation, the lice were placed on a patch which was placed on a second patch that was on top of a slide warmer maintained at 37° C. Lice not dead or morbid (unable to move towards heat 1 hour after treatment; sickly, but not necessarily dying; may recover by 24 hours), will move to the lower patch. Lice again were examined for their ability to move towards 24 hours later. 2% α-butyl cinnamic aldehyde provided 100% knockdown at the 1 hour time point and 98.6% mortality at 24 hours, while there was no mortality associated with treatment of water.

Example 11

Effect of Cinnamic Aldehyde Formulations on Adult Lice and Louse Eggs

Adult Lice

Adult human lice (*Pediculus humanus*) were treated with one of four different formulations to determine their pediculicidal activity. Formulation 1 was 10% α-hexyl CNMA (AHCNMA) plus 1% saponin. Formulation 2 contained 10% AHCNMA plus 1% saponin plus shampoo. Formulation 3 contained 2% α-butyl CNMA (ABCNMA) plus 1% saponin. Formulation 4 contained 2 ABCNMA plus 1% saponin plus shampoo. For each of four replicates per treatment, 25 mixed sex lice were placed in a 9 dram plastic vial and covered with a screened plunger to keep the lice from floating to the surface. The vial containing the lice was dipped into a 100 ml beaker containing the respective treatments, or distilled water as a negative control. Lice were submerged in the treatments for 10 minutes. After this time, the test container was removed from the treatment, submerged in a 1000 mL beaker containing distilled water (32° C.) for 1 minute and agitated, then washed again in distilled water (32° C.) from a wash bottle. Subsequently, lice were allowed to recover in an incubator maintained at 31.70° C. in 60% RH (relative humidity) for 1 hour. Following the recovery period, lice were examined for their ability to move towards heat as described in Example 20. As shown below, each of the treatment effectively killed lice (24 hour observation) after a 10 minute treatment with the formulation, while there was no mortality associated with treatment with water. The results are shown in Table 7, below.

TABLE 7

Effect of Cinnamic Aldehyde Formulation on Human Lice

| Treatment[3] | Total Lice | Number Killed | Number Moribund[2] | % Mortality |
|---|---|---|---|---|
| 1 | 62 | 62 | 0 | 100 |
| 2 | 50 | 47 | 0 | 94 |
| 3 | 58 | 51 | 4 | 93.1 |
| 4 | 59 | 51 | 6 | 96.6 |
| Control[1] | 60 | 2 | 1 | 5 |

[1]Control = water treated lice
[2]Moribund = unable to move towards heat 24 hours after treatment
[3]Treatment 1 = 10% α-hexyl CNMA (AHCNMA) plus 1% saponin
Treatment 2 = 10% AHCNMA plus 1% saponin plus shampoo
Treatment 3 = 2% α-butyl CNMA (ABCNMA) plus 1% saponin
Treatment 4 = 2% ABCNMA plus 1% saponin plus shampoo Louse Eggs Louse eggs (*Pediculus humanus*) were treated with three different formulations to determine the ovicidal activity of the compounds. Formulation 1 was 10% α-hexyl CNMA (AHCNMA) plus 1% saponin. Formulation 2 contained 10% AHCNMA plus 1% saponin plus shampoo. Formulation 3 contained 2% α-butyl CNMA (ABCNMA) plus 1% saponin. For each of three replicates per treatment, 400–500 louse eggs were placed in a vial and covered with a screened plunger to keep the eggs from floating to the surface. The vial containing the eggs was dipped into a 100 ml beaker containing the respective treatments, or distilled water as a negative control. Eggs were submerged in the treatments for either 10 minutes (formulations 1 and 2) (Table 8) or for 30 minutes (formulation 3) (Table 9). After this time, the test container was removed from the treatment, submerged in a 1000 mL beaker containing distilled water (32° C.) for 1 minute and agitated, then washed again in distilled water (32° C.) from a wash bottle. Subsequently, the louse eggs were examined for their ability to hatch. As shown below, formulations 1 and 2 were moderately ovicidal, while formulation 3 (2% α-butyl CNMA (ABCNMA) plus 1% saponin) at 10 minutes killed 35.3% of the eggs and at minutes completely prevented eggs from hatching.

TABLE 9

Effect of Cinnamic Aldehyde Formulations of Louse Eggs (Experiment 2)

| Treatment[2] | Total eggs | Hatched eggs | Half-hatched eggs | Un-developed eggs | % Mortality | % Un-developed |
|---|---|---|---|---|---|---|
| Formula 1 | 523 | 393 | 26 | 29 | 24.9 | 5.5 |
| Formula 2 | 402 | 350 | 12 | 22 | 12.9 | 5.5 |

TABLE 9-continued

Effect of Cinnamic Aldehyde Formulations of Louse Eggs (Experiment 2)

| Treatment[2] | Total eggs | Hatched eggs | Half-hatched eggs | Un-develop-eggs | % Mortality | % Un-developed |
|---|---|---|---|---|---|---|
| Formula 3 | 484 | 0 | 0 | 437 | 100 | 90.3 |
| Control[1] | 425 | 379 | 3 | 29 | 10.5 | 6.6 |

[1]Control = water treated eggs
[2]Treatment 1 = 10% α-hexyl CNMA (AHCNMA) plus 1% saponin
Treatment 2 = 10% AHCNMA plus 1% saponin plus shampoo
Treatment 3 = 2% α-butyl CNMA (ABCNMA) plus 1% saponin

Example 12

Production of Aromatic Aldehydes in Microbial Systems

A cDNA library is generated using RNA extracted from six week old tobacco stems. 20 μg of polyA RNA is prepared and cDNA synthesized. Part of this is cloned into lambda-ZAP II vector (a commercially available cloning vector). At least 500,000 recombinants are screened using an oligonucleotide probe designed from peptide sequence sequences of CCoAr protein purified from six week old tobacco stem tissue using the protocol of Goffner, et al., *Plant Physiol.* (1994) 106:625. Strongly hybridizing clones are selected and used to rescreen the cDNA library. The resulting clones are sequenced to enable the identification of full-length cDNA inserts and the introduction of appropriate CCoAR gene sequences into yeast expression vector pMTL8110 (Faulkner, et al (1994) *Gene* 143:13–20. The coding sequences for *Rhodosporidium toruloides* phenylalanine ammonia lyase (PAL; GenBank locus RHDPAL) and a parsley 4-coumarate:CoAl ligase (4CL; GenBank locus PC4CL1AA) are similarly introduced into equivalent yeast expression vectors. The PAL,4CL and CCoAR constructs are used to transform *Saccharomyces cerevisiae* strains by electroporation using established published procedures (Becker, and Guarente, *Methods in Enzymology* 194:182–187, 1991; Simon, (1993) *Methods in Enzymol* 217:478–483. Transformants are selected on minimal medium lacking leucine. Transformant strains carrying all three gene constructs are identified by PCR and selected for further analysis.

Extracts from both transformed and untransformed control strains are used for determinations of PAL, 4CL and CCoAR enzyme activities using well established published assays. Strains in which the activity of PAL, 4CL and CCoAR is significantly greater than the background activity detected in control strains are selected for further analysis. Selected strains are analyzed for aromatic aldehyde production using standard published procedures and those producing significant amounts of cinnamaldehyde are selected for optimization of fermentation conditions.

Example 13

Treatment of Corn Root Worm with Cinnamic Aldehyde and with Tween 80 and/or NaHCO3

Plant Foliar Bioassay

Plants are grown in 7.5 mm pot in potting soil in greenhouse. Corn plants are used for corn root worm. When plants reach 3 leaf stage, they are infested with 60 of the specified anthropod (6 replications). The corn root worm is allowed to settle and feed. The plant is sprayed to runoff (about 5 ml) with a formulation containing 100 to 2000 ppm, or 0.1 to 2 g/l concentration of a test formulation. The plant is draped with plastic covering to prevent the formulation from touching the soil. The mortality of the worms after three, five and seven days on the plants sprayed with a test formulation is determined and compared with that of worms on plants sprayed only with water and/or a formula blank.

Example 14

Treatment of Russian Wheat Aphid with Cinnamic Aldehyde and with Tween 80 and/or NaHCO3

Plant Foliar Bioassay

Plants are grown in 7.5 mm pot in potting soil in greenhouse. Wheat plants (Kansas variety) are used for Russian wheat aphid. When plants reach 3 leaf stage, they are infested with 60 of the specified anthropod (6 replications). The insect is allowed to settle and fee. The plant is sprayed to runoff (about 5 ml) with a formulation containing 100 to 10,000 ppm, or 0.1 to 10 g/l concentration of a test formulation. The plant is draped with plastic covering to prevent the formulation from touching the soil. The mortality of the insects after 36 hours, five days and seven days on the plants sprayed with the test formulation is determined and compared with that of insects on plants sprayed only with water and/or a formula blank.

Example 15

Treatment of Thysanoptera with Cinnamic Aldehyde and with Tween 80 and/or NaCHO3

Plant Foliar Bioassay

Plants are grown in 7.5 mm pot in potting soil in greenhouse. Rose plants of various varieties are used for aphids. When plants reach 3 leaf stage, they are infested with 60 of the specified anthropod (6 replications). The insect is allowed to settle and feed. The plant is sprayed to runoff (about 5 ml) with a formulation containing 100 to 10,000 ppm, or 0.1 to 10 g/l concentration of a test formulation. The plant is draped with plastic covering to prevent the formulation from touching the soil. The mortality of the insects after 36 hours, five days and seven days on the plants sprayed with the test formulation is determined and compared with that of insects on plants sprayed only with water and/or a formula blank.

Example 16

Treatment of Melon Aphid

Plant Foliar Bioassay

Treatment of melon aphid (*Aphis gossypii Glover*) is conducted as follows. Plants were grown in 7.5 mm pots in planting soil in greenhouse. Chrysantemums (*c. morifolum*) were used for melon aphid plant foliar bioassays.

A. Treatment of Flowering Plants with Cinnamaldehyde

Flowering plants were infested and pre-count population size for each plant were taken and number of mean of aphids nymphs per leaf calculated. The plants were sprayed to runoff (about 5 ml) with an aqueous formulation containing 1,000 ppm, 3,000 ppm, and 10,000 ppm concentration of cinnamic aldehyde, and a negative control containing only $H_2O$. After 36 hours, the number of insects on the leaves sprayed with a given test formulation was determined and compared with that of insects on leaves sprayed with negative control only. Mean aphid nymphs per leaf were determined to be less than 10 for each cinnamic aldehyde concentration compared to a pre-count mean of about 60. See Table 6.

TABLE 6

Effect of Cinnamic Aldehyde on Melon Aphid

| Formulation | Mean Number of Aphid Nymphs Per Leaf |
|---|---|
| CNMA (ppm) | |
| 1,000 | 6 ± 3 |
| 3,000 | 4 ± 3 |
| 10,000 | 1 ± 1 |
| Control | |
| H$_2$O | 33 ± 11 |
| Pre-count | 60 |

*CNMA = cinnamic aldehyde (ppm) in H$_2$O.

B. Treatment of Plants with Cinnamaldehyde and Saponin

Whole nonflowering potted chrysanthemum plants were used to assay melon aphids. Two plants were treated for each treatment and two leaves, one from the top of the plant and one from the bottom of the plant, were sampled to determine the number of living and dead melon aphids. Three treatments were applied: 1.0% CNMA plus 0.5% saponin, 0.5% CNMA plus 0.25% saponin, and 0.5% saponin only. The whole plants were sprayed to "drip" on both the top and bottom sides of leaves. Results are presented as the proportion of aphids found dead. Results were as follows: control plant (0.5% saponin only) 14.8% ±4.5; 0.5% CNMA 48.3±16.1; 1.0% CNMA 72.0±11.2.

These results indicate the CNMA alone or with saponin can kill a high degree of aphids with direct applications.

Example 17

Treatment of Spiders

Contact treatment

To determine the contact activity of the formulae, test arachnids Latrodectus spp and *Laxosceles reclusa* are directly sprayed. The treated spiders are carefully removed and placed in untreated petri dishes or vials. Five different concentrations of each active ingredient in a formula are directly sprayed onto the test spider. A formula blank and a negative control are tested. Five replicates are tested with each formula and spider. Mean mortality of spiders are determined for each treatment at 24 and 48 hours.

Example 18

Treatment of Scab Mite

Contact Treatment

Scab Mite (or Psoroptic Scab)(*Psoroptes equi* (Raispail) and *P. ovis* (Hering)) are tested to determine the contact insecticidal activity of the subject formulae. Test mites are directly sprayed with a given test formula. Treated mites are removed and placed in untreated petri dishes or vials. Five different concentrations of each active ingredient in a formula are directly sprayed onto the test scab mite. A formula blank and a negative control also are tested. Five replicates are tested for each formula. Mean mortality of mites are determined at 24 and 48 hours for each treatment.

Example 19

Treatment of Bed Bug

Contact Treatment

To determine the contact activity of the cinnamaldehyde (CNMA) and alpha hexyl cinnamaldehyde (AHCNMA) formulae, test bed bugs (*Cimex lectularis*) are directly sprayed with a given test formulation. The treated bed bugs are removed and placed in untreated petri dishes or vials. Five different concentrations of each active ingredient in a formula are directly sprayed onto the test bed bug. As a control, a formula blank and a negative control (H$_2$O) are tested. Mean mortality of bed bugs are counted at 24 and 48 hours for each treatment.

Example 20

Residual Activity of Cinnamaldehyde and α-hexyl Cinnamaldehyde

Two separate experiments indicated that both cinnamaldehyde (CNMA) and alpha hexyl cinnamaldehyde (AHCNMA) have residual activity. In the first experiment, two ml of two concentrations of CNMA (0.3 and 1%) were sprayed on filter paper (Whatman). As a negative control, two ml of water was also sprayed on filter paper. Twenty-four hours later, two ml of water were sprayed on treatment and control filter paper, which were then dried for 30 min. Approximately 30 thrips insects (*Frankliniella occidentalis*) were introduced onto the treated filter papers and the number of *F. occidentalis* were observed after one hour. Mean mortality was calculated for each treatment. After 72 hours, the treated filter papers were flipped over and only the negative control filter paper and the filter paper treated with 1% CNMA were sprayed with 2 ml of water and allowed to dry for 30 minutes. Approximately 30 thrips were introduced onto the two treated filter papers and after one hour the number of dead *F. occidentalis* were observed and the mean mortality calculated for each treatment. A similar assay was conducted using AHCNMA. Mean mortality was higher for rehydrated filter papers compared to non-rehydrated filter papers over time. These experiments demonstrate that rehydration plays a role in the continued lethal effects of treated filter paper in contact with thrips.

Continuous Exposure Tests

To further determine the residual activity of CNMA and AHCNMA, insects are confined to deposits on two representative surfaces. Glass is used to represent non-porous surfaces and filter paper is used as a porous surface. Two ml of five different concentrations of each active ingredient in a formula are applied to filter paper disks (9 cm diameter) or the bottoms of glass petri dishes (9 cm diameter). As a control, two ml of formula minus active ingredient are also applied. The deposits are allowed to dry for 24 hours before testing. At test intervals of 7, 14, 28, and 56 days, one set of plates and filter papers are rehydrated with 2 ml of water, while a parallel set is not rehydrated. Insects are then confined to the deposits continuously and the number of insects killed by the deposits is counted regularly. If deposits fail to kill insects within 48 hours, these treatments are discontinued from further aging studies.

Example 21

Control of Mealybugs

Contact Treatment

To determine the contact activity of the cinnamaldehyde (CNMA) and alpha hexyl cinnamaldehyde (AHCNMA) formulae, test mealybugs are sprayed directly with a given test formulae. The treated insects are removed and placed in sterile untreated petri dishes or vials. Five different concentrations of each active ingredient in a formula are directly sprayed onto the test mealybug. As a control, a formula blank and a negative control (H$_2$O) are tested. Five replicates are tested with each formula. Mean mortality of mealybugs is determined for each treatment at 24 and 48 hours.

The above results demonstrate that formulations containing aromatic aldehydes, as exemplified by cinnamic aldehyde, are effective in killing pests including disease carrying insects, insects and arachnids.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now having been fully described, it will be apparent to one of ordinary skill in the art that many changes and modifications can be made thereto without departing from the spirit or scope of the appended claims.

What is claimed is:

1. A method for decreasing the population of ants in an area, said method comprising:

contacting said ants, their food supply or their habitat with an aqueous composition comprising about 0.1 to 5.0% α-hexyl cinnamic aldehyde to decrease the population of said ants.

* * * * *